United States Patent [19]
Andersen et al.

[11] Patent Number: 5,656,732
[45] Date of Patent: Aug. 12, 1997

[54] POLYPEPTIDES OF FELINE T-CELL LYMPHOTROPHIC LENTIVIRUS

[75] Inventors: Philip R. Andersen, Portland; Thomas P. O'Connor, Westbrook; Quentin J. Tonelli, Portland, all of Me.

[73] Assignee: IDEXX Laboratories, Inc., Westbrook, Me.

[21] Appl. No.: 306,539

[22] Filed: Sep. 15, 1994

Related U.S. Application Data

[63] Continuation of Ser. No. 120,311, Sep. 13, 1993, abandoned, which is a continuation of Ser. No. 447,810, Dec. 8, 1989, abandoned, which is a continuation of Ser. No. 348,784, May 8, 1989, abandoned, which is a continuation of Ser. No. 293,906, Jan. 5, 1989, Pat. No. 5,219,725, which is a continuation of Ser. No. 279,989, Dec. 5, 1988, abandoned.

[51] Int. Cl.$^6$ .................................................. C07K 14/15
[52] U.S. Cl. .................. 530/395; 424/188.1; 424/208.1; 530/388.35; 530/412; 530/413
[58] Field of Search .......................... 424/148.1, 160.1, 424/188.1, 208.1; 435/69.1, 69.3, 172.3, 240.2, 252.3, 252.33, 320.1; 514/8; 530/388.35, 395, 412, 413

[56] References Cited

U.S. PATENT DOCUMENTS

| | | | |
|---|---|---|---|
| 4,514,505 | 4/1985 | Canfield et al. | 436/500 |
| 5,037,753 | 8/1991 | Pedersen et al. | 435/235.1 |
| 5,177,014 | 1/1993 | O'Connor et al. | 435/188 |

FOREIGN PATENT DOCUMENTS

WO90/06510   6/1990   WIPO.

OTHER PUBLICATIONS

Robey et al., "Characterization of Envelope and Core Structural Gene Products of HTLV–IV With Sera From AIDS Patients," *Science* 228:593–595, 3 May 1985.

Robey et al., "Prospect For Prevention of Human Immunodeficiency Virus Infection: Purified 120–KDA Envelope Glycoprotein Induces Neutralizing Antibody," *Proc. Natl. Acad. Sci. USA* 83:7023–7027, Sep. 1986.

Pyle et al., "Purification of 120,000 Dalten Envelope Glycoprotein From Culture Fluids of Human Immunodeficiency Virus (HIV)–Infected H9 Cells," *AIDS Res. Hu. Retrovirus* 3(4):387–400, 1987.

Matsudaira, P., "Sequence From Picomde Quantities of Proteins Electroblotted Onto Polyvinylidene Difluoride Membranes," *J. Biol. Chem* 262(21):10035–10038, 25 Jul. 1987.

Olmsted et al., "Nucleotide Sequence Analysis of Feline Immunodeficiency Virus: Genome Organization and Relationship to Other Lentiviruses," *Proc. Natl. Acad. Sci. USA*. 86:8088–8092, Oct. 1989.

Shaw et al., "Molecular Characterization of Human T–Cell Leukemia (Lymphotropic) Virus Type III in the Acquired Immune Deficiency Syndrome", *Science* 226:1165–1171, 7 Dec. 1984.

Lerner, R.A., "Tapping the Immunological Repertoire to Produce Antibodies of Predetermined Specificity," *Nature* 299:592–596, 14 Oct. 1982.

Braun et al., *Virology* 167:515–523 (1988).

Olmsted et al., "Molecular Cloning Of Feline Immunodeficiency Virus", *Proc. Natl. Acad. Sci USA* 86:2448 (1989).

Egberink et al., "Intracellular Proteins Of Feline Immunodeficiency Virus And Their Antigenic . . . " *J. General Virology* 71:739–743 (1990).

Steinman et al., "Biochemical And Immunological Characterization Of The Major Structural Proteins Of Feline Immunodeficiency Virus", *J. General Virology* 71:701–706 (1990).

Hellström et al., "Monoclonal Anti–melanoma Antibodies and Their Possible Clinical Use", *Monoclonal Antibodies for Cancer Detection and Therapy*; pp. 19–51 (1985).

Voller, "The Enzyme Linked Immunosorbent Assay (ELISA)", 2 *Diagnostic Horizons*; 1–7 (1978).

Pederson et al., "Isolation of a T–lymphotropic Virus From Domestic Cats With an Immunodeficiency–Like Syndrome", 235 Science 790, 1987.

O'Connor et al., "Characterization of the Major Structured Proteins of Feline T–Lymphotropic Lentivirus (FTLV)" *J. Clin. Micro.* p. 213, Mar. 1989.

Harbour et al., "Isolation of a T–lymphotropic Lentivirus From A Persistently Leucopenic Domestic Cat," *Veterinary Record*, 122:84–86 (1988).

The Veterinary Record, "Implications of the Isolation of FTLV," vol. 122, No. 4, (1988).

Wilson et al., "Recent Developments in the Periodate Method Conjugating Horseradish Peroxidase," North Holland Biomedical Press, pp. 215–223 (1978).

Hardy "Feline T–lymphotropic Lentivirus: Retrovirus–Induced Immunosuppression in Cats," Journal of the American Animal Hospital Assoc., pp. 241–243, vol. 24, 1988.

UC Glip Sheet (TRENDS) 1987.

Sparger, "Feline T–Lymphotrophic Lentivirus Infection," Feline Medicine IV; Veterinary Learning System, 1988 pp. 9–14.

Talbott et al., "Nucleotide Sequence and Genomic Organization of Feline Immunodeficiency Virus," 86 P.N.A.S. USA 5743–5747, Aug. 1989.

Olmsted et al. "Nucleotide Sequence Analysis of Feline Immunodeficiency virus: Genome Organization and Relationship to Other Lentiviruses." 86 P.N.A.S. (USA) 8088–8092 (Oct. 1989).

*Primary Examiner*—Robert D. Budens
*Attorney, Agent, or Firm*—Fish & Richardson P.C.

[57] ABSTRACT

Purified polypeptides of Feline Immunodeficiency Virus (FIV) are disclosed. The polypeptides of the invention include p10, p15, p26, gp40, gp100 and gp130.

3 Claims, 6 Drawing Sheets

IBI Pustell Sequence Analysis Programs
Ver 2.02 Copyright J.Pustell 1987-1989
Mon Apr 3,1989 - 3:19 PM
Translation Analysis of 10CXXL3

Translation of 10CXXL3 over region 3-202.

```
            10              20              30              40              50
             *               *               *               *               *
AA GAT GAA CAA GGA GTA GCA AAA AGC AAA GAA GTC AAA GAA CTG CTA ACG TAT GTT
TT CTA CTT GTT CCT CAT CGT TTT TCG TTT CAG TTT CTT GAC GAT TGC ATA CAA
Asp Glu Gln Gly Val Ala Lys Ser Lys Val Lys Glu Leu Leu Thr Tyr Val
          a___a___a___a___AUTOTRANSLATION OF 10CXXL3_a___a___a___a___
  b___b___b10_b___b___b_b20b___10CXCON__0_b___b___b_b40_b___b___b_b_b50b___

60              70              80              90             100
             *               *               *               *               *
TTG TTG ATA CAA CTC TCA TAA TAT AAA TTT ATA ATG AAC ACA TCG GCA AAA ATC
AAC AAC TAT GTT GAG TTA ACA AGT ATT TTT TCC TGT TAC TTG TGT AGC CGT TTT TAG
Leu Leu Ile Gln Leu Ser End Lys Tyr Lys Met Asn Thr Ser Ala Lys Ile
          a___a___a___a___AUTOTRANSLATION OF 10CXXL3_a___a___a___a___
  b___b___b70_b___b___b_b_b___10CXCON___b___b___b_b_90_b___b___b_b100_b___

110             120             130             140             150
             *               *               *               *               *
TAT CTA ACT CAT AAG TTA ACA AGG AAA CCA GTG TTG CTA CCG ATT CTA AGA
ATA GAT TGA GTA TTC AAT TGT TCC TTT CAC AAC GAT GGC TAA GAT TCT
Tyr Leu Thr His Lys Leu Thr Arg Lys Pro Val Leu Leu Pro Ile Leu Arg
          a___a___a___a___AUTOTRANSLATION OF 10CXXL3_a___a___a___a___
  b110b___b___b_b120_b___b___10CXCON___b___b___b_b140_b___b___b150_b___

160             170             180             190             200
             *               *               *               *               *
ATT CCC CTG GCT GCT CGG GAG CGC GCC CNC GGA GGG GAA TTC AGT GC
TAA GGG GAC CGA GCG ACC CTC GCG GNG CCT CCC CTT AAG TCA CG
Ile Pro Leu Ala Ala Arg Glu Arg Ala Xxx Gly Gly Glu Phe Ser Ala
          a___a___a---a-AUTOTRANSLATION OF 10CXXLB---a---a---a---a--
  160_b___b___b170b___b___b_10CXCON_b___b___b_190_b___b___b200b___
```

FIG. 5a

```
IBI Pustell Sequence Analysis Programs
Ver 2.02 Copyright J.Pustell 1987-1989
      Mon Apr 3,1989 -  3:25 PM
        Translation Analysis of 2BYCXL2
---------------------------------------------------
Translation of 2BYCXL2 over region 2-163.

10          20          30          40          50
           *           *           *           *           *
  G GAT CCT GAC CGG CAC CGT GCC CGT CCC TTG TGC CCT CAA CTN AGC CTG TCG GGG AGA
  C CTA GGA CTG GCC GTG GCA GGG AAC ACG GGA GTT GAN TCG GAC AGC CCC TCT
    Asp Pro Asp Arg His Arg Pro Leu Cys Pro Gln Leu Ser Gly Arg)
  ___a___a___a___a___AUTOTRANSLATION OF 2BYCXL2_a___a___a___a___)
  <_b160_b___b___b___150_b___b___b___1_2BYCON___b130b___b___120_b___b___

60          70          80          90         100
           *           *           *           *           *
  CCA CTG CCC TGC TGT GGG TTC GGC GCC TGG AAC TTC CTG GGA CCT AAC CCT
  GGT GAC GGG ACA CCC AAG CCG ACA CCG CGG ACC TTG AAG GAC CCT GGA TTG GGA
  Pro Leu Pro Cys Cys Gly Phe Gly Ala Trp Asn Phe Leu Gly Pro Asn Pro)
  ___a___a___a___a___AUTOTRANSLATION OF 2BYCXL2_a___a___a___a___)
  <110_b___b___b100b___b___9_2BYCON___b80_b___b___b___b_70b___b___

110         120         130         140         150
           *           *           *           *           *
  AAC CCT AAG CCC TAC CCC GAA CCG GAC CCT GGA GAC CTG AAA NCT AAC GCC TGC
  TTG GGA TTC GGG ATG GGG CTT GGC GGA GGG GAC TTT NGA TTG CGG ACG
  Asn Pro Lys Pro Pro Tyr Pro Glu Pro Asp Pro Gly Asp Pro Leu Lys Xxx Asn Ala Cys)
  ___a___a___a___a___AUTOTRANSLATION OF 2BYCXL2_a___a___a___a___)
  <60__b___b___b___b_50_b___b___b___b_40_2BYCON___30__b___b___b20_b___b___b_10

160
           *
  CTC GAT CCC
  GAG CTA GGG
  Leu Asp Pro)
  (---a---a---)
  (___b___b___
```

FIG. 5b

```
IBI Pustell Sequence Analysis Programs
Ver 2.02 Copyright J.Pustell 1987-1989
       Mon Apr 3,1989 - 3:14 PM
    Translation Analysis of R5XCXL1
```

Translation of R5XCXL1 over region 1-172.

```
              10            20            30            40           50
     *     *     *     *     *     *     *     *     *     *
GCG ACC AAC TCC CAA TCG TGC GAA AAT GTA TTC TCG AGT NAC CTG CCA AAT
CGC TGG TTG AGG GTT AGC ACG CTT TTA CAT AAG AGC TCA NTG GAC GGT TTA
Ala Thr Asn Ser Gln Ser Cys Glu Asn Val Phe Ser Ser Xxx Leu Pro Asn)
___a___a___a___a___AUTOTRANSLATION OF R5XCXL1_a___a___a___a___a___)

60            70            80            90          100
     *     *     *     *     *     *     *     *     *     *
GGA CAC AAC ACA GTT TGG GAA CAG GTG GTC TTT CCT CTN AGT ATT TTT TGG
CCT GTG TTG TGT CAA ACC CTT GTC CAC CAG AAA GGA GAN TCA TAA AAA ACC
Gly His Asn Thr Val Trp Glu Gln Val Val Phe Pro Leu Ser Ile Phe Trp)
___a___a___a___a___AUTOTRANSLATION OF R5XCXL1_a___a___a___a___a___)

110           120           130           140          150
     *     *     *     *     *     *     *     *     *     *
GAT CTA TTT NTN AGA GTG AGA AAT TGT GTG TTG ACG TCC CTT TTT CCT TTT
CTA GAT AAA NAN TCT CAC TCT TTA ACA CAC AAC TGC AGG GAA AAA GGA AAA
Asp Leu Phe Xxx Arg Val Arg Asn Cys Val Leu Thr Ser Leu Phe Pro Phe)
___a___a___a___a___AUTOTRANSLATION OF R5XCXL1_a___a___a___a___a___)

160           170
     *     *     *     *
AGG GAT CTG GTC ATA TTC T
TCC CTA GAC CAG TAT AAG A
Arg Asp Leu Val Ile Phe)
___a___a___AUTOTRANSLATION OF__a___)
```

FIG. 5c 5,656,732

POLYPEPTIDES OF FELINE T-CELL LYMPHOTROPHIC LENTIVIRUS

This is a continuation of application Ser. No. 08/120,311, filed Sep. 13, 1993, now abandoned; which is a continuation of 07/447,810, filed Dec. 8, 1989, now abandoned; which is a continuation of 07/348,784, filed May 8, 1989, now abandoned; which is a continuation of 07/293,906, filed Jan. 5, 1989, now U.S. Pat. No. 5,219,725; which is a continuation of 07/279,989, filed Dec. 5, 1988, now abandoned.

This invention was made with government support under Grant AI-27605 awarded by the National Institutes of Health. The government has certain rights in the invention.

BACKGROUND OF THE INVENTION

This invention relates to purification of polypeptides from feline T-cell lymphotropic lentivirus (FIV).

FIV is a retrovirus originally isolated from cats which exhibit an AIDS-like syndrome. Pederson et al., 235 Science 790, 1987. The virus belongs to the same group as the human immunodeficiency virus (HIV), the causative agent of human AIDS. Pederson et al., describe detection of antibody to FIV by an immunofluorescent assay, and by Western blots, using virus purified by centrifugation on sucrose gradients in Tris base, pH 7.4, containing 0.1M NaCl and 1 mM EDTA. A few protein bands were detected and, although antigenic comparison was not made, the positions of these bands were tentatively said to correspond to the major core protein, p24 the gag precursor protein, p55, and the endonuclease protein, p32, of, HIV.

Pederson et al., U.S. Pat. No. 5,037,753 entitled "Feline T-Lymphotropic Lentivirus" (which is not admitted to be prior art to the present application) describes the results presented by Padarson et al., supra, and states that Western blotting of FIV infected cell lysates yielded major protein bands at approximately 22–26 kD, usually about 24 kD; 50–60 kD, usually about 55 kD; and 28–36 kD, usually about 32 kD.

SUMMARY OF THE INVENTION

In a first aspect, the invention features a purified polypeptide having an epitope of an antigenic polypeptide of FIV. The polypeptide may be glycosylated or unglycosylated. By antigenic polypeptide is meant a polypeptide which is able to raise (with the aid of an adjuvant if necessary) an antibody response in cats. The polypeptide may be a polypeptide fragment of at least 5 amino acids, or a polypeptide naturally occurring in FIV particles. The fragment may be obtained from a naturally-occurring polypeptide, for example, by enzymatic digestion of a naturally occurring polypeptide, or may be produced by isolation or synthesis of a gene encoding a desired polypeptide and expression of that polypeptide within a desired expression system, for example, a bacterial, yeast, or mammalian expression system.

By epitope is meant a single antigenic site of an antigenic polypeptide. Such an epitope is recognized specifically by a monoclonal antibody to an antigenic polypeptide of FIV.

By purified is meant that the polypeptide is separated from other cell components with which it naturally occurs, for example, FIV polypeptides. Preferably, the polypeptide is sufficiently pure to permit its use to prepare a monoclonal antibody to the polypeptide, and even more preferably, pure enough to allow the amino acid sequence of the polypeptide to be determined by standard procedure. Generally, the purified polypeptide is biologically active in that it is suitable for preparation of a monoclonal antibody, or is suitable for detection of naturally-occurring antibodies within the serum of a cat.

In preferred embodiments, the purified polypeptide has at least 75% amino acid homology to a polypeptide fragment of at least 20 amino acids obtained from an FIV gag or env polypeptide, most preferably the purified polypeptide includes an amino acid sequence having at least 75% homology to a whole of a gag or any polypeptide, even more preferably, the purified polypeptide is an entire gag or env amino acid sequence. Examples of gag and env polypeptides include p10, p15, p26, gp40, gp100, and gp130.

In a second aspect, the invention features a method for detecting an antibody to FIV within a sample, including the steps of providing a purified polypeptide as described above, and contacting that polypeptide under conditions suitable to allow an antibody/polypeptide complex to form between antibodies within the sample and the purified polypeptide, and detecting the formation of such complexes. The presence of antibody/polypeptide complexes is indicative of antibody to FIV present within the sample.

In a third aspect, the invention features a purified nucleic acid including a 50 nucleotide sequence having at least 90% homology with a 50 nucleotide sequence naturally occurring in an FIV particle. By purified is meant that the nucleic acid is substantially separated away from all of the components with which it naturally occurs, e.g., polypeptides and other nucleic acids. Preferably, the nucleic acid is completely separated from such components, and is a pure solution of nucleic acid, or is held within a cell in which it does not naturally occur, e.g, a bacterial cell, another viral particle or a non-feline eucaryotic cell. By 90% homology is meant that the nucleotide sequence is identical at at least 45 of the 50 nucleotides.

In preferred embodiments, the nucleic acid encodes a polypeptide including an epitope of an antigenic polypeptide of FIV, e.g., an epitope of a gag or env polypeptide of FIV. Most preferably the nucleic acid is carried in an expression vector and can be expressed in a bacterial, fungal or other eucaryotic cell, e.g., a mammalian cell.

In a related aspect the invention features purified polypeptide including ten or more contiguous amino acids taken from the sequence (using standard letters to represent amino acids) V-Q-S-R-G-S-G-P-V-C-F-N-C-K-K-P-G-H-L-A-R-Q-S-H or P-I-Q-T-V-N-G-V-P-Q-Y-V-A-L-D-P-K-M-V-S or S-V-Q-S-R-G-Q-G-P-V-A-F-N.

Applicants have provided polypeptides suitable for specific detection of FIV antibodies and thus have allowed accurate detection of infection with FIV. Applicants have also provided polypeptides useful for production of vaccines to prevent disease caused by FIV in cats.

Other features and advantages of the invention will be apparent from the following description of the preferred embodiment thereof, and from the claims.

DESCRIPTION OF THE PREFERRED EMBODIMENTS

The drawings will first briefly be described.

Drawings FIG. 1 is a photograph of the major vital associated proteins of FIV identified by polyacrylamide gel electrophoresis (PAGE) and stained with Commassie Blue R250 (lane A); molecular weight standards are shown in lane B;

FIGS. 5A–5C show the nucleic acid sequence, and coresponding amino acid sequence, of various portions of cloned FIV nucleic acid.

Antigenic FIV Polypeptides

Figure 1:
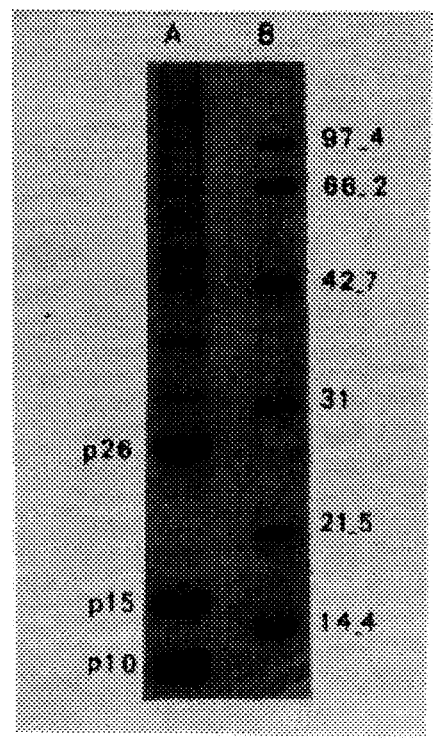

FIV polypeptide antigens useful in this invention are generally described above. Polypeptides useful in this invention may be purified from virus isolated as described below and fragments of the purified polypeptides isolated by enzymatic treatment or other standard procedures. Further, the polypeptides may be synthesized by standard in vitro expression systems in which DNA encoding for the FIV polypeptide is cloned and expressed in a bacterial, yeast, or mammalian cell expression system. Such DNA may be isolated and expressed as described below. The polypeptides may also be synthesized by standard chemical methods, for example, the polypeptide segments of various FIV polypeptides given below can be synthesized. In the following example FIV polypeptides were obtained directly from FIV-infected cells and took the form of polypeptides naturally occurring in an FIV virus particle. This example is not limiting to the present invention, and those skilled in the art will recognize the many alternative methods for obtaining polypeptides of this invention. The polypeptides are referred to according to molecular weight, thus a polypeptide of 30 kD is termed p30, and a glycoprotein of this weight is termed gp30.

Master seed virus producing cultures were obtained in the form of a continuous feline cell line infected with FIV isolate #2427 (CRFK-FIV or Petaluma strain) from Dr. Nails Pederson (University of California, Davis, Calif.). The parent cell line is Crandell feline kidney cell persistently infected with FIV. The cell line was deposited with the American Type Culture Collection on Jul. 13, 1988 and assigned the number CRL9761. Applicants and their assignees acknowledge their responsibility to replace this culture should it die before the end of the term of a patent issued hereon, 5 years after the last request for a culture, or 30 years, whichever is the longer, and its responsibility to notify the depository of the issuance of such a patent, at which time the deposit will be made irrevocably available to the public. Until that time the deposit will be made available to the Commissioner of Patents under the terms of 37 C.F.R. §1–14 and 35 U.S.C. §112.

Other virus cultures can be obtained as described by both Pederson et al. references, supra, or by Harbour et al., 122 The Veterinary Record 84, 1988. Seed stocks of virus producing cell cultures were obtained by freeze-downs of FIV-infected master seed cell cultures following at least 19 post infection passages in culture. Additional seed stocks of virus producing cultures were obtained by either infection of the continuous feline cell culture with FIV master seed virus or by single cell microwell cloning of high level FIV producers from the original FIV infected master seed cell culture. For propagation, master seed virus infected feline cell cultures were inoculated into tissue cell culture flasks. Following growth to a confluent monolayer of cells, tissue culture fluid was harvested at intervals of 2–5 days.

Working seed virus was produced by propogation by the master seed cell line permanently infected with FIV. An inoculum was added to tissue culture flasks, in Dulbecco's Modified Eagles medium containing 2 mM L-glutamine and 4.5 g per liter/glucose (DME) containing 100 units per ml. penicillin and streptomycin and 2 mM glutamine. An inoculum was added to tissue culture flasks, incubated, and the spent tissue culture fluid harvested when the cells were grown to confluence. The cells were released from the culture vessel with trypsin/EDTA and diluted between 1:5 and 1:25 (typically 1:8) in medium. Typically the flasks were incubated at 36° C.–38° C. for a maximum of 7 days (between 3 and 7 days) before fluid and cell harvest. The harvested fluid, including cell material, was centrifuged in a high speed centrifuge (Sorval RC-5B or Beckman J2-21) leading to separation of supernatant and cell pellet material. The cell pellet was discarded, and the supernatant culture fluid used to prepare working virus. The clarified supernatant was made 0.5M in NaCl and 4%–10% (usually 7%) in polyethylene glycol (PEG 8000, Sigma). Following overnight incubation at 2° C. –7° C., virus was pelleted (at 13,000×g for 30 min.) a confluent monolayer of cells, tissue culture fluid was harvested at intervals of 2–5 days.

Working seed virus was produced by propogation by the master seed cell line permanently infected with FIV. An inoculum was added to tissue culture fupernatant centrifuged on a 50%/80% discontinuous glycerol step gradient in 10 mM Tris 300 mM NaCl, 1 mM EDTA at pH 7.6. Centrifugation was at 100,000×g for 3 hrs. at 4° C. and the FIV viral band at the 50%–80% interface collected. The band was suspended in 10 mM Tris, 0.3 M NaCl and 1 mM EDTA and diluted 1:3 in the buffer and repelleted at 100,000×g for 1 hr. The resulting pellet was purified virus and was resuspended in the above buffer and stored at −70° C. The resulting virus was substantially free from FIV host cell proteins and was composed of at least 5% p26 (the major nucleocapsid protein, as measured by densitometric scans of Commassie Blue 250 stained SDS/PAGE as total protein).

Such purified virus may be obtained by other techniques, however, applicants have found that high molecular weight contaminants present in virus preparations may be eliminated by use of the high salt (i.e., greater than physiological range salt concentration) used in the gradient centrifugation procedure.

Referring to FIG. 1, polypeptides associated with purified FIV were analyzed by SDS/PAGE and compared with polypeptides isolated in an identical manner from the spent culture medium of uninfected cells. Analysis of the Commassie Blue stained gels revealed three major polypeptides with molecular weights of about 10, 15, and 26 kD, named p10, p15 and p26, respectively.

When an ELISA test was performed using disrupted FIV to identify cats possessing polyclonal antibody to FIV polypeptides, and Western blot analysis then performed on feline sera determined to be positive by ELISA, each of the cats had antibodies which reacted with one or more polypeptides of molecular weight p10, 15, 26, 40 and 65 kD under the conditions used.

Figure 2:
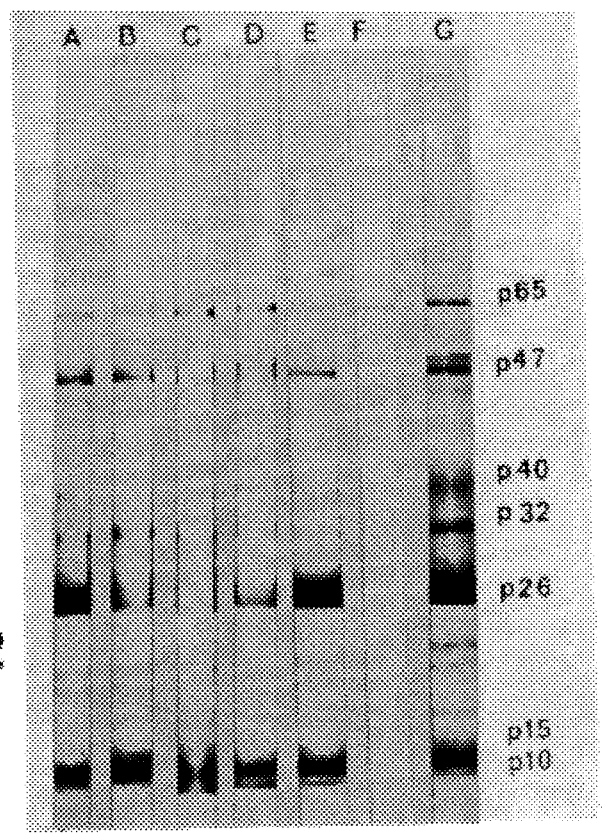
FIG. 2 is a photograph of a Western immunoblot analysis of antibodies to FIV found in serum from cats identified as positive by an ELISA assay for FIV antibodies.

Referring to FIG. 2, a standard Western immuno blot was performed as described by Towbin et al., 76 Proc. Natl. Acad. Sci USA 4350, 1979. Briefly, FIV was disrupted with SDS and proteins transferred to a sheet of nitrocellulose. The nitrocellulose sheet was blocked with 30% calf serum, 1% bovine serum albumin (BSA), and 0.05% Tween 20 in Dulbecco's phosphate buffer saline. The sheets were cut into 0.5 cm strips and incubated with a 1:100 dilution of serum sample in blocking buffer for 2 hrs. for 20°–22° C. Strips were repeatedly washed with washing buffer (0.05% Tween 20 in Dulbecco's phosphate buffer saline) and then incubated with a second antibody (specific for feline heavy and light chain Ig) horseradish peroxidase conjugate (obtained from Kirkguard and Perry Laboratories Inc. Gaithersburg, Md.). After 1 hr. incubation, the strips were repeatedly washed with washing buffer and incubated with the precipitating substrate 4-chloronaphthol for 10 min. The strips were partially dried and the results interpreted immediately. The serum in each of the lanes A–G was obtained from various cats infected with FIV. Predominant cross-reactivity is detected with p26 and p15 and to a lesser extent with p10. Other proteins of 32, 40, 47 and 65 kD molecular weight are also detected.

Certain vital polypeptides, such as the gag (e.g., p26) antigenic polypeptides, are abundant in purified viral preparations, others such as the viral envelope polypeptides (e.g., gp130) tend to be lost during viral purification, and electrotransfer less efficiently for Western blot analysis than the gag antigens. Therefore, in order to more readily detect the viral envelope (env) and the gag precurser polypeptides, FIV cell extracts were labeled with $^{35}$S-methionine and cysteine and examined by immunoprecipitation (RIPA). Confluent cultures of cells infected with FIV were incubated for 30 min. in methionine and cysteine-free Dulbecco's modified Eagle's medium. The cell cultures were then incubated for 4 hrs. in 8 ml of the same medium containing 100 microCuries per ml of $^{35}$S-methionine and $^{35}$S-cysteine (specific activity 1200 Curies per mM, New England Nuclear Corporation, Boston, Mass.). The radioactive tissue culture fluids were removed and the cells lysed with 5 ml of 10 mM sodium phosphate buffer pH 7.5 containing 100 mM NaCl 1% Triton X 100, 0.5% sodium deoxycholate, 0.1% SDS, 0.1 mM phenylmethylsulfonylfluoride, and 100 Kallikren inactivator units of aprotenin per ml. (Sigma Chemical Co., St. Louis, Mo.). Before use, the cell lysates were clarified by centrifugation 100,000×g for 30 min. and the pellet discarded. Aliquots of the labelled cell lysates (0.1 ml) and 5 µl of serum being tested were mixed in a microcentrifuge tube and incubated for 1 hr. at 37° C. and then overnight at 4° C. The next day, 0.2 ml of a 5% suspension of protein A Sepharose CL-4B beads (Pharmacia, Piscataway, N.J.) in 10 mM of phosphate buffer, pH 7.5 containing 100 mM NaCl, 1 % Triton X-100 and 0.1% SDS was added to each tube and mixed for 30 min. at 4° C. The antibody/antigen complexes bound to the protein A Sepharose beads were collected by centrifugation (2 min. at 20,000×g) and washed 3 times in lysing buffer. The final pellet was resuspended in 25 µl SDS/PAGE loading buffer and heated and 100° C. for 3 minutes. The Sepharose beads were removed by centrifugation and the supernatant applied to a PAGE. Gels were processed for fluorography using enlightening™ (New England Nuclear Corporation, Boston, Mass.) and exposed at –70° to Kodak XR-5 film. Sera from experimentally infected cats recognize polypeptides of 15, 22, 36, 40, 47, 110 and 130 kD. Although there were some quantitative and qualititative differences all cats appear to mount a response to p22, gp40, gp47 and gp130.

In order to determine which of the polypeptides identified by RIPA-PAGE analysis were related to the major internal structural protein, p26, RIPA-PAGE analysis was carried out using monoclonal antibodies which reacted with p26 as determined by Western blotting. This monoclonal immunoprecipitated proteins p47, p36, p22 and p15. High molecular weight polypeptides (130 kD) of FIV which were not detected by the p26 specific monoclonal antibody, were identified by RIPA-PAGE. A protein of molecular weight 100 kD was also detectable utilizing serum antibodies obtained from some infected cats.

In another example, antigenic glycopeptides of FIV can be obtained as follows. Actively growing CRFK FTLV infected cells were scraped from roller bottles, gently washed with phosphate-buffered saline (PBS), and pelleted. The cell pellet was gently resuspended in 10 mM sodium phosphate, pH 7.2, at a ratio of 1 ml buffer to 0.1 ml of cell pellet. This suspension was incubated on ice or refrigerated for 5–10 min., vigorously vortex mixed for 30 seconds, and four volumes of PBS with 1 mM PMSF added. The mixture was then vigorously homogenized for 90–120 seconds with a Brinkmann Homogenizer PT10/35 with a PTA 20 generator.

The resulting homogenate was clarified for 20 minutes at 5,000×g. The supernatant fraction was discarded and the cell membrane pellet resuspended in PBS+0.2% Triton X-100 at a ratio of 2.5 ml buffer to 0.1 ml original cell pellet. The mixture was then vigorously homogenized for 90–120 seconds with a Brinkmann Homogenizer PT 10/35 with a PTA 20 generator. The resulting homogenate was clarified at 100,000×g for 1 hr, the supernatant decanted off and batch bound overnight at 20°–23° C. on Pharmacia Lentil Lectin Sepharose 4B at a ratio of 6 ml of resin to 5 ml of original cell pellet.

The Lentil Lectin Suspension was poured through a column, the resin collected, and washed with 15 column volumes of PBS+0.2% Triton X-100. The glycoproteins were then eluted from the resin by subjecting the resin to 5–10 column volumes of PBS+0.2% Triton X-100+200 mM methyl α-D mannopyranoside, collecting fractions of 1 column volume/tube.

The isolation of glycoproteins was verified by 9% SDS-PAGE electrophorisis, and checked using $^{35}$S-radiolabeled cell preparations in conjunction with RIPA data.

Further purification of viral glycoprotein from host cell glycoprotein includes use of HPLC, or of a polyclonal or monoclonal antibody for affinity chromatography.

EXAMPLE 1: gag Polypeptide Purification

Isolated virus (250–500 microliters) was combined with two volumes of 6M guanidine hydrochloride, pH 3 (adjusted with 20% trifluoro acidic acid in water). The mixture was vortexed and incubated at 37° C.–40° C. in a water bath for 20–25 minutes. The incubated solution was filtered through a pre-wetted (100 microliters of 6M guanidine hydrochloride, pH 3) 0.45 micron gel aquadisk filter (No. 4184) and the filter rinsed with 100 microliters of 6M guanidine hydrochloride pH 3. The filtered sample was loaded onto an HPLC column for purification.

The HPLC system consisted of a Beckman HPLC having three 110 V pumps, a 421 controller, a 166 variable wavelength detector, a 427 integrator, a 210A injector with dynamic mixer, and a 1000 microliter sample. The column was a Waters radial compression cartridge held in an RCM-100 column holder with a modified inlet connector (Waters MicroBond-A-Pak Fenile 10 MU 8 mm ×10 cm cartridge No. 85722 with a guard pak resolve CN cartridge, No. 85826). The system was set such that two levers were compressed and the pressure was in the mid-yellow zone.

Purification was by a multi-step gradient from aqueous 0.1% trifluoroacetic acid (v/v solvent A) to aceto nitrol containing 0.1% trifluoroacetic acid (v/v, solvent B).

Fractions were collected and condensed by a Savant Speed Vac to remove all solvents to a final volume ranging from 50–100 microliters. The condensed fractions where neutralized by addition of 200–300 microliters of 50 mM or 100 mM sodium phosphate buffer, pH 7.2. The buffered fraction pHs were then checked with pH paper and, if the pH was still below 6, 1N NaOH added until the pH was brought within the range of 6.5–7.5. The neutralized fractions were frozen at –20° C. until use.

Figure 3:
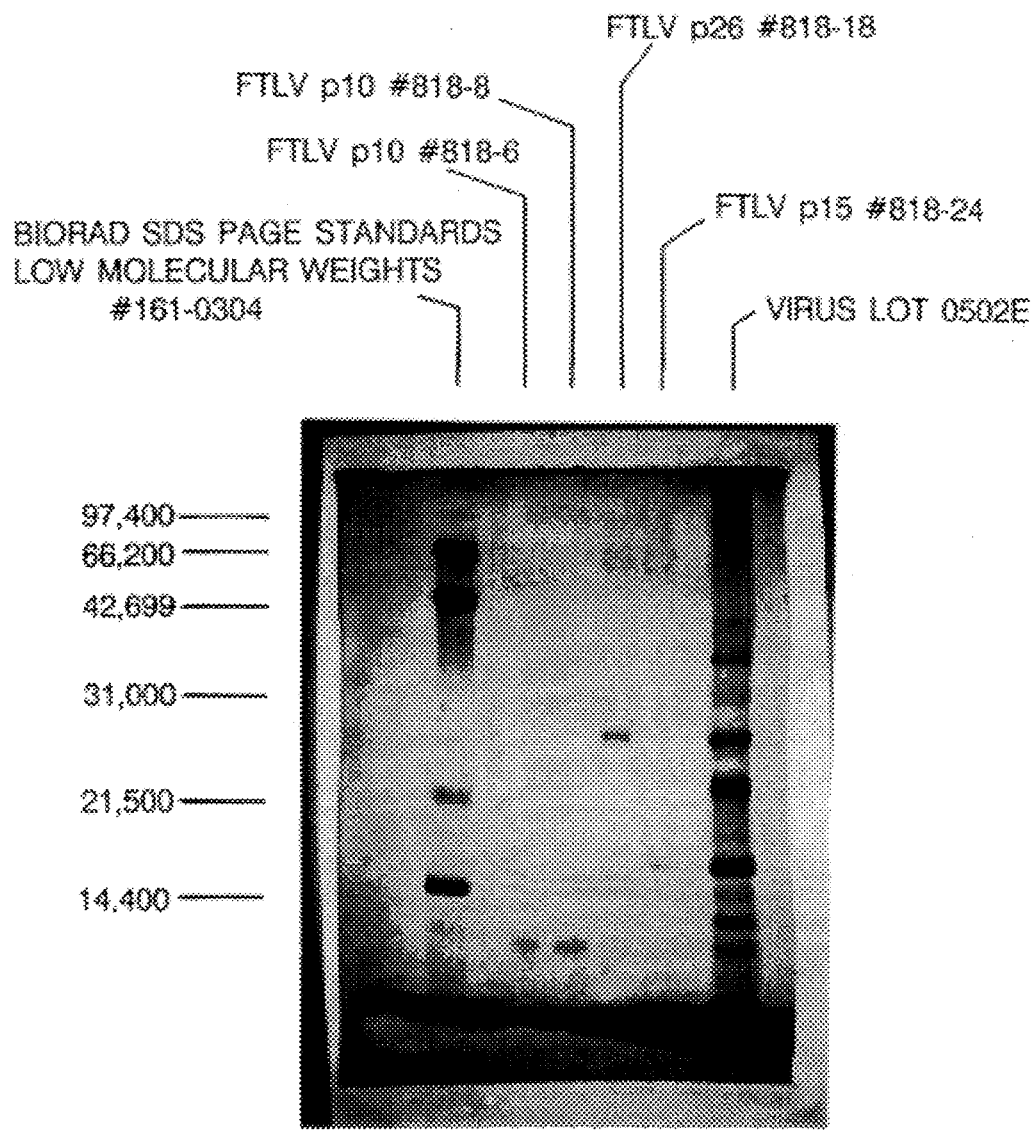
FIG. 3 is a graphical representation of elution of FIV polypeptides during HPLC purification.

Referring to FIG. 3, the printout from an HPLC column described above is shown. The flow rate was at 1 ml per minute starting with 100% of solvent A. After 15 min. the solvent was changed to contain 26% solvent B, 10 min. later to 31% solvent B, 12 min. later to 37.5% solvent B, 5 min. later to 40% solvent B, 6 min. later to 43% solvent B, 8 min. later to 45% solvent B, 15 min. later to 60% solvent, and 20 min. later to 100% solvent B. Peaks corresponding to p10, p15, and p26 are indicated in FIG. 3. Fractions containing these peaks were collected.

Figure 4:
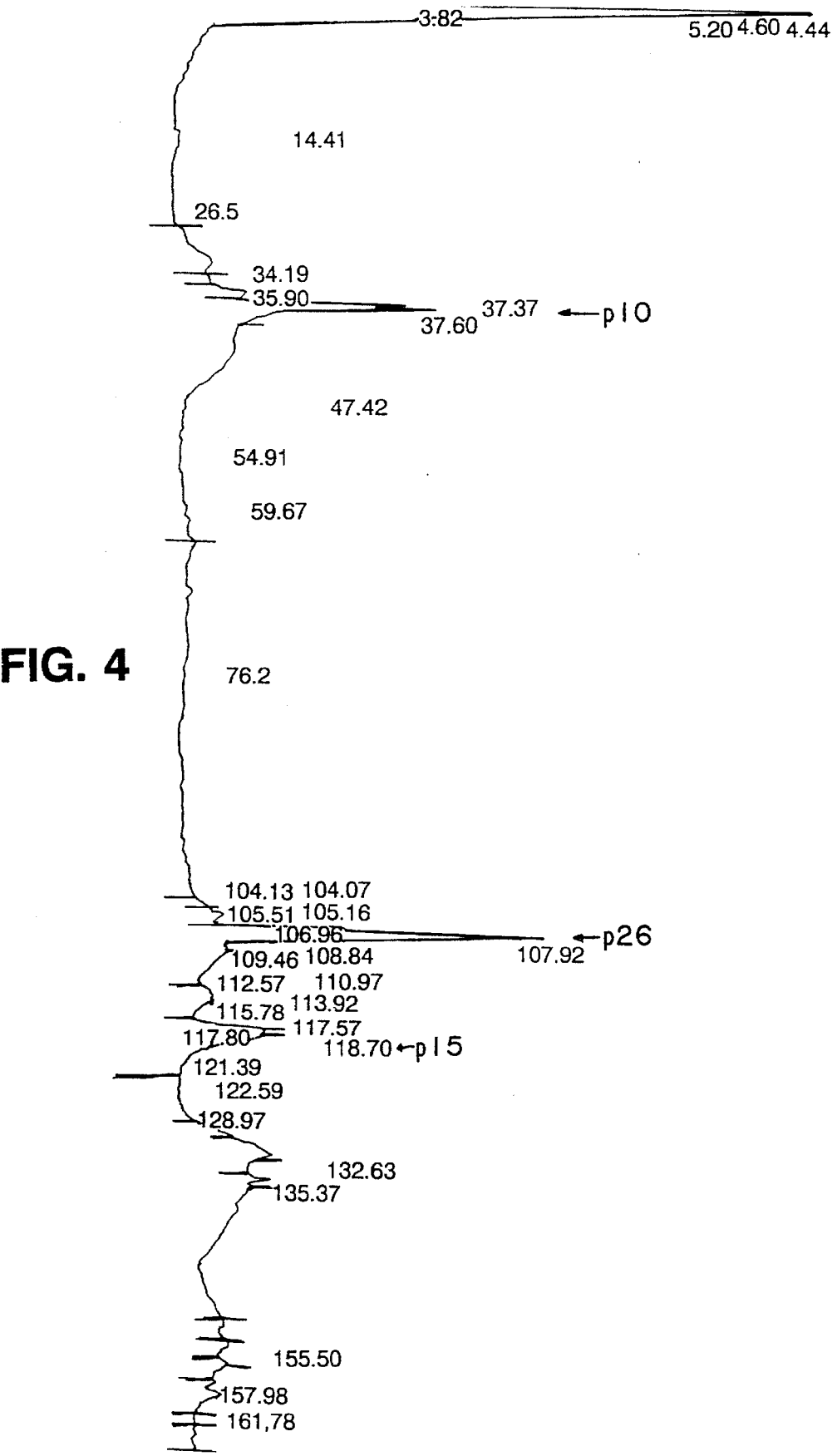
FIG. 4 is a photograph of an SDS-polyacrylamide gel after electrophoresis and staining with silver, showing purity of various FIV polypeptides.

Referring to FIG. 4, fractions corresponding to p10, p15 and p26 were run in an SDS-polyacrylamide gel containing 15% bis-acrylamide at 70 V. The gel was stained with silver using a Biorad Silver Staining Kit 161-0443. The isolated fractions corresponding to p15, p10, and p26 were essentially homogeneous solutions of the FIV polypeptides.

The isolated FIV polypeptides were analyzed by standard technique for their amino acid sequence, yielding the following results (? indicates uncertainty in the actual amino acid, or no knowledge at all).

p26

| Number | 1-2-3-4-5-6-7-8-9-10-11-12-13-14-15-16-17-18-19-20 |
|---|---|
| Amino Acid | P-I-Q-T-V-N-G-V-P- Q- Y- V- A- L- D- P- K- M- V- S | p10

| Number | 1-2-3-4-5-6-7-8-9-10-11-12-13-14-15-16-17-18-19- |
|---|---|
| Amino Acid | V-Q-S-R-G-S-G-P-V- C- F- N- C- K- K- P- G- H- L- |
| Number | 20-21-22-23-24 |
| Amino Acid | A- R- Q- S- H |

P15

| Number | 0-1-2-3-4-5-6-7-8-9-10-11-12-13 |
|---|---|
| Amino Acid | S-V-Q-S-R-G-Q-G-P-V- A- F- N- ? |

In order to determine if the purified polypeptide is useful in this invention, that is, whether the polypeptide is antigenic, any standard procedure can be used. For example an ELISA test can be performed using a polyclonal antibody from cat serum to determine whether the polypeptide is cross-reactive. Alternatively, the polypeptide can be injected with or without an adjuvant, into an animal, e.g., a mouse, to determine if it causes antibodies to be raised to it. These polypeptides are useful for production of vaccines to prevent FIV-caused disease symptoms and FIV infection in cats. These vaccines are produced by standard procedure. Preferably the gag or env polypeptides are provided in a standard inoculation medium and injected intravenously, intrarterially or otherwise into a cat at a level of 1–100 μg/kg animal at intervals of 3–4 weeks until immunity to FIV is produced.

FIV Monoclonal Antibodies

Antibodies to FIV polypeptides are useful aids for identification of a purified polypeptide (as described above), and for purifying polypeptides. They are also useful to determine the antigenicity of any polypeptide. An example of preparation of useful antibodies follows. These antibodies are monoclonal antibodies which allow specific detection and purification of either individual or a small number of FIV polypeptides.

Balb/CJ (Jackson Labs) mice were immunized with an initial injection of 50 micrograms of FIV virus (prepared as described above) per mouse mixed 1:1 with Difco Bacto adjuvant complete. After two weeks a booster injection of 100 micrograms of FIV virus was injected into each mouse intravenously without adjuvant. Three days after the booster injection a fusion was performed with mouse myeloma cell lines FO or p3X63-Ag8.653. Mid log phase myeloma lines were harvested on the day of fusion and checked for viability. The cells were spun at 300×g for 8 min., separated from the growth medium, and resuspended in serum free DME.

For fusion, an FIV-inoculated mouse was killed by cervical dislocation and the spleen aseptically removed. The spleen was washed three times in serum free DME and placed in a sterile Petri dish containing 20 mls of complete medium (DME containing 20% bovine fetal serum, 100 units per ml. of penicillin and streptomycin, and 1 mM sodium pyruvate). To release cells, the spleen was perfused with a 23 gauge needle.

Cells were placed in a 50 ml conical centrifuge tube and pelleted at 300×g for 8 min. The pellet resuspended in 5 ml of 0.17M ammonium chloride and placed on ice for 8 min. 5 ml of bovine fetal serum (20%) was added and the cells pelleted again at 300×g for 8 min. After resuspension in 10 ml DME the cells were counted and the spleen and myeloma cells mixed in a ratio of 3:1. The cell mixture was pelleted at 200×g for 10 minutes, the supernatant decanted, and the pellet allowed to stand for 5 min. Over a period of 1 min., 1 ml of 50% PEG (PEG 1500 mixed 1:1 with Hepes pH 8.1) at 37° C. was added. After 1 min. incubation at 37° C., 1 ml of DME was added over a period of another 1 min. and then a second 1 ml of serum free medium added over a period of 1 min. Finally, 10 mls of DME was added over a period of 2 min., the cells pelleted at 200×g for 8 min., and the pellet resuspended in complete medium containing 0.016 mM thymidine, 0.1 mM hypoxanthine, 0.5 micromolar aminopterin, and 10% hybridoma cloning factor (1×HAT). The cells were plated into 96-well plates.

After 3, 5 and 7 days half of the medium in the fusion plates was removed and replaced with fresh 1×HAT. After 11 days the hybridoma cell supernatant was screened by an ELISA test. In this test, 96 well plates were coated with FIV virus by standard technique. One hundred microliters of supernatant from each well was added to a corresponding well on a screening plate and incubated for 1 hr. at 20°–22° C. After incubation, each well was washed three times with distilled water and 100 microliters of a horseradish peroxidide conjugate of goat anti-mouse IgG (H+L), A, M (1:1500 dilution) was added to each well and incubated for 1 hr. at 20°–22° C. After three washes with distilled water, the substrate OPD/hydrogen peroxide was added and incubation continued for five to fifteen minutes. One hundred microliters of a stop solution (1M hydrochloric acid) was then added and the absorbance at 490 nm read. Cultures which had an optical density reading greater than the control wells were removed to 2 cm² culture dishes, with the addition of normal mouse spleen cells in 1×HT medium. After a further three days all of the 2 cm² cultures were rescreened for antibody and those testing positive again were cloned by limiting dilution. The cells in each 2 cm² culture were counted and cell concentration adjusted to 1×10⁵ cells per ml. The cells were diluted in complete medium and normal mouse spleen cells at concentrations of hybridoma cells of 5, 10 and 50 cells per ml added. The cells were plated into 96-well plates for each dilution. After 10 days the cloning plates were screened for growth. About 37% of all wells showed growth. The growth-positive wells were screened for antibody and those testing positive expanded to 2 cm² cultures and provided with normal mouse spleen cells. The cloning procedure was repeated 2 times until a stable antibody-producing hybridoma was obtained. At this point the cell culture was expanded from 2 to 9 to 75 to 150 cm² culture vessels, at which point ascite production could be commenced.

For ascites production, pristane primed IRCF1 female mice were used. 0.5 ml of pristane was injected intraperitoneally (IP) to each mouse, and the mouse allowed to rest for 10–60 days. At this time $4.5 \times 10^6$ cells were injected IP into each mouse and ascites formed in 7–14 days. Ascites fluid was harvested with a pasteur pipette through a hole in the peritoneum.

Antibodies to glycoproteins can also be isolated and detected. In particular, antibodies to two glycoproteins of molecular weight 40 kD (gp40) and 130 kD (gp130) which are detected using PAGE and RIPA respectively.

Monoclonals useful in this invention for purification and identification of specific polypeptides of FIV include those which are specific for FIV and form a sufficiently strong interation with an FIV epitope, and an FIV antigen, to be useful in an immunoassay, for example, an ELISA, to detect an FIV antigen. In order to determine which of the above monoclonal antibodies are useful in this invention one main test was used. This entailed determination of whether the monoclonal antibody can bind FIV antigen and be detected with a conjugate of polyclonal antibody to FIV (an ELISA test, described above).

Another test is to perform a Western blot to determine whether the monoclonal antibody has good reactivity with one or more FIV antigens. Generally, those monoclonals which show poor reactivity, that is, produce faint bands on the Western blot, are not suitable in this invention. Yet another test involves radioimmunoprecipitation assay (RIPA) where FIV virus labeled with $^{35}$S-methionine is reacted with a monoclonal antibody to form within immunoprecipitate, and the immunoprecipitate run in a SDS-PAGE and autoradiographed to detect the labelled proteins. This analysis determines which of the monoclonal antibodies is able to detect precursor FIV antigenic polypeptides and not just mature polypeptides.

Antibody Detection

The above antigenic polypeptides can be used to detect naturally occurring antibodies produced by cats. Such detection can be any standard immunoassay procedure, for example, by an ELISA test, as described above. One example of such a test follows. This example is not limiting to the present invention and those skilled in the art will recognize that any of many other standard procedures can be used.

EXAMPLE 2: Antibody assay

Materials required to perform this assay include 96 well flat bottom microtiter strips coated with a solution containing the appropriate test antigen (e.g., p26, p15, or p10). The test wells were coated with 100 µl of a solution containing 0.15 micrograms antigen in 0.25 molar sodium citrate, pH 7.5. The wells were covered with parafilm, incubated overnight at 4° C., and tapped until dry. The antigen was then overcoated by adding 200 µl 1% BSA in 0.25 molar sodium citrate, incubating at room temperature (20°–25° C.) for 1 hour, and tapping the wells dry. 200 microliters of 7.5% sucrose in 0.25 molar sodium citrate was then added to each well and incubated at room temperature for 30 minutes. The resulting strips were used immediately, or dried under vacuum for 6 hours at room temperature for later use.

Assays were performed by adding 100 µl of feline serum sample (positive control, negative control, or test sera) diluted 1 to 100 in Dulbecco's PBS containing 0.1% Bovine serum albumin, 30% calf serum, and 0.05% Tween-20 (Sigma Chemical, St. Louis, Mo.) to a well, incubating at room temperature for 30 minutes, and tapping the well dry. The wells were washed immediately two times with Dulbecco's PBS containing 0.05% Tween-20, tapping the wells dry after the second wash.

100 µl of a solution containing antibodies to feline immunoglobulin was then added. These antibodies were conjugated to an indicator enzyme (e.g., alkaline phosphatase) and then dissolved in a solution of 50% fetal calf serum, 0.05% Tween-20 in 0.05M Tris-HCl, pH 7.6. The wells were incubated at room temperature for 30 minutes, tapped dry, and then washed two times with Dulbecco's PBS containing 0.05% Tween-20.

A solution containing 0.1% 3,3',5,5' Tetramethylbenzidene in 40% Glycerol and 60% methanol was mixed with an equal volume of a solution containing 22.82 grams dibasic potassium phosphate, 19.2 grams citric acid and 1.34 milliliters 30% hydrogen peroxide solution per liter. One hundred microliters of this solution was added to each well, and then incubated at room temperature for 15 minutes. At the end of the incubation period, 100 µl of 0.25% hydrofluoric acid was added to each well. The optical density at 650 nanometer of the solution in each well was then determined with a microtiter plate reader. An immune response to p10, p15 and p26 was detectable either following experimental infection of a cat with FIV, or in feline sera possessing antibodies to FIV.

FIV Nucleic Acid

FIV nucleic acid is useful for production of large amounts of FIV polypeptides, or fragments thereof, and also for detection of homologous nucleic acid in vivo, using standard techniques. There follows an example of cloning of FIV viral DNA. The specific FIV strain chosen is not meant to be limiting in this invention and those skilled in the art will recognize that equivalent nucleic acid may be isolated by use of the cloned sequences which are provided as specific deposits, or by techniques similar to those described in this example.

A Crandal feline kidney cell line productively infected with FIV strain 2428 (Pentaluma isolate) was used as a source of unintegrated viral DNA. The unintegrated vital DNA was prepared by Hirt extraction and CsCl-ethidium bromide centrifugation to resolve linear and supercoiled viral DNA. (Hirt, 26 J Mol. Biol. 365, 1967; Canaani et al., 282 Nature 378, 1979).

The supercoiled viral DNA was used to construct libraries which contain overlapping viral DNA sequences. The procedures used to construct these libraries were similar to those described by Maniatis et al., Molecular Cloning, A Laboratory Manual, Cold Spring Harbor Lab, Cold Spring Harbor, N.Y.) and Glover, DNA Cloning, Vol. 1, A Practical Approach, IRL Press, Washington, D.C.) and are familiar to those of ordinary skill in the art.

Two vital DNA libraries were generated by cleavage of supercoiled vital DNA by one of two restriction endonucleases. Partial cleavage by the restriction endonuclease RsaI, which recognizes the DNA sequence 5'GTAC3', or cleavage by the restriction endonuclease HaeIII, which recognizes the DNA sequence 5'GGCC3', of the supercoiled viral DNA generates two sets of blunt-ended DNA molecules whose sequences overlap. The blunt-ended DNA molecules were then treated with EcoRI methylase, according to the manufacturer's directions, to modify the 3' adenine residue of the EcoRI recognition sequence 5'-GAATCC-3'. Methylation at this site inhibits the cleavage of treated DNA by the restriction endonuclease EcoRI. The methylated DNA molecules were then ligated to linker DNA molecules which contained a cleavage site for the restriction endonuclease EcoRI. The linker containing DNA molecules were then treated with the restriction endonuclease EcoRI to generate molecules whose termini were compatible with the EcoRI cloning site in the recombinant DNA phage vector λ ZAP™ (Stratagene, La Jolla, Calif.). Linker fragments resulting from this cleavage were separated from the large DNA molecules by size separation on a quickspin column (Boehringer, Mannheim, Indianapolis, Ind.). The DNA molecules were then ligated into the EcoRI cleaved λ ZAP vector using T4 DNA ligase (New England Biolabs, Beverly, Mass.). Ligated DNA molecules were then packaged into phage using Gigapack gold (Stratagene, La Jolla, Calif.). Viable phage from the packaging reaction were then amplified by infecting BB4 cells (Stratagene) and harvesting plate lysates of those infected cells in order to obtain a stock of recombinant λZAP clones.

Because the insert DNA of the recombinant λZAP clones contain host cellular DNA as well as FIV proviral DNA sequences, it was necessary to screen each library with an FIV DNA probe that contains a readily detectable label. Such a probe was made from RNA isolated from FIV. A radioactive complementary DNA was synthesized from total viral RNA essentially as described by Maniatis et al. 1982, supra except that selection of poly A-containing RNA was not performed, and methymercuric hydroxide was omitted from the protocol.

The bacteriophage libraries were plated at a density of 10,000 bacteriophage per 150 mm dish. They were then screened by hybridization of the radioactively labeled probe to phage DNA which was immobilized on nitrocellulose filters (Maniatis, et al., 1982 supra). Each hybridizing bacteriophage plaque was then picked, replated, and hybridized as described, until a single well was isolated which contained a λZAP recombinant clone. XL-1-Blue cells (Stratagene) were then infected with recombinant λZAP phage, and plasmids containing the insert DNA were obtained following superinfection with R408 helper phage according to the manufacturer's directions (Stratagene, La Jolla, Calif.). This procedure also provides both recombinant plasmids (which can be isolated from the cell) and single stranded phage stock which can be isolated from the medium for DNA sequence analysis.

The above recombinant plasmids were analyzed for inserts by preparing plasmid DNAs from overnight culture of bacteria replicating these plasmids as follows. One and one half ml. of an overnight culture was placed in a microcentrifuge tube and spun for four minutes at 4000×g. The supernatant was removed and the tube respun for four minutes at 4000×g. The supernatant was removed and the tube respun for a few seconds, and residual liquid removed carefully with a pasteur pipet. The bacterial pellet was then thoroughly resuspended in 200 microliters of a solution contaiing 8% sucrose, 50 mm EDTA, 5% Triton X-100 and 50 MM Tris/HCl, pH 8.05. 20 microliters of a lysozome solution at a concentration of 10 milligrams lysozyme per milliliter in 10 millimolar Tris/HCl, pH 8 and one millimolar EDTA was then added, mixed, and the mixture was incubated at 4° C. for 15 minutes. The solution containing bacteria was then placed in a boiling water bath for 90 seconds. The mixture was chilled on ice, and spun in a microfuge in the cold for 10 minutes at 11,000×g. The pellet was carefully removed with a glass pipet. Ice cold isopropanol (200 microliters) was then added, the solution thoroughly mixed, and incubated at −20° C. for 5 minutes. The chilled solution was centrifuged at −20° C. at 11,000×g for 10 minutes to pellet the plasmid DNA. The supernatant was carefully removed and the pelleted DNA briefly air dried. The DNA pellet was then dissolved in 100 microliters of sterile double distilled water. Plasmid DNAs thus isolated were anlayzed for inserts by restriction enconuclease cleavage and electrophoresis in 0.8% agarose gels (Maniatis et al., 1982 supra).

Standard dideoxy sequence analysis was performed on the recombinant DNA containing clones. Single stranded phage were isolated from the media used to propagate cells containing the bluescript plasmid using the method generally described in the M13 dideoxy sequencing manual published by Bethesda Research Laboratories (Gaithersburg, Md.). A number of clones were sequenced and analyzed by this method. Sequence information for clones termed 10CX, 2BY, and R5X is presented in FIG. 5a, b, and c along with the putative translated amino acid sequence for each clone. These amino acid sequences show homology with the amino acid sequence of the envelope gene of equine infectious anemia virus, a lentivirus, immunologically closely related to FIV.

Nucleic acid probes derived from the 2BY DNA sequence hybridize to DNA isolated from FIV infected but not uninfected cells. These probes can be used to isolate other FIV genes from other strains and can be expressed by standard procedures to provide the purified polypeptides described above.

Deposit

Strains 10CX, 2B4 and R5X have been deposited with the ATCC (12301 Parklawn Drive, Rockville, Md. 20852) and assigned numbers 67937, 67938, and 67939, respectively.

Applicants' and their assignees acknowledge their responsibility to replace these cultures should they die before the end of the term of a patent issued hereon, 5 years after the last request for a culture, or 30 years, whichever is the longer, and its responsibility to notify the depository of the issuance of such a patent, at which time the deposits will be made irrevocably available to the public. Until that time the deposits will be made available to the Commissioner of Patents under the terms of 37 CFR Section 1–14 and 35 USC Section 112.

Other embodiments are within the following claims.

We claim:

1. Purified and isolated FIV gp40.
2. Purified and isolated FIV gp100.
3. Purified and isolated FIV gp130.

* * * * *

UNITED STATES PATENT AND TRADEMARK OFFICE
CERTIFICATE OF CORRECTION

PATENT NO. : 5,656,732
DATED : August 12, 1997
INVENTOR(S) : Andersen et al.

It is certified that error appears in the above-identified patent and that said Letters Patent is hereby corrected as shown below:

Page 1, in the left column, under the heading "Related U.S. Application Data", please correct the paragraph to read:

This is a continuation of application Ser. No. 08/120,311, filed Sept. 13, 1993, now abandoned; which is a continuation of 07/447,810, filed Dec. 8, 1989, now abandoned; which is a continuation-in-part of 07/348,784, filed May 8, 1989, now abandoned; which is a continuation-in-part of 07/293,906, filed Jan. 5, 1989, now U.S. Patent No. 5,219,725; which is a continuation-in-part of 07/279,989, filed Dec. 5, 1988, now abandoned.

Signed and Sealed this

Seventh Day of August, 2001

*Attest:*

*Attesting Officer*

NICHOLAS P. GODICI
*Acting Director of the United States Patent and Trademark Office*